United States Patent [19]

Cauwet et al.

[11] Patent Number: 5,449,475
[45] Date of Patent: Sep. 12, 1995

[54] COMPOSITIONS FOR CONDITIONING KERATINOUS SUBSTANCES BASED ON ALKYL POLYGLYCOSIDES AND THEIR USE FOR THE WASHING AND CONDITIONING OF HAIR

[75] Inventors: Danièle Cauwet, Paris; Claude Dubief, Le Chesnay, both of France

[73] Assignee: L'Oreal, Paris, France

[21] Appl. No.: 169,661

[22] Filed: Dec. 20, 1993

[30] Foreign Application Priority Data

Dec. 18, 1992 [FR] France ................... 92 15676

[51] Int. Cl.$^6$ .................. C11D 3/37; C11D 1/86; C11D 3/22
[52] U.S. Cl. .................. 252/174.23; 252/174.17; 252/173; 252/547; 252/549; 252/541; 252/174.21; 252/174.11; 252/DIG. 5; 252/DIG. 13; 514/881
[58] Field of Search .............. 252/174.17, 174.23, 252/547, DIG. 5, DIG. 13; 514/880, 881

[56] References Cited

U.S. PATENT DOCUMENTS 4,668,422  5/1987  Mauk et al. ............... 252/174.17
4,772,462  9/1988  Boothe et al. ............. 424/70

FOREIGN PATENT DOCUMENTS 0203750 12/1986 European Pat. Off. .
0269243  6/1988 European Pat. Off. .
0337354 10/1989 European Pat. Off. .
0521748  1/1993 European Pat. Off. .
0531650  3/1993 European Pat. Off. .
4134019  5/1992 Japan .

*Primary Examiner*—Paul Lieberman
*Assistant Examiner*—Lorna M. Douyon
*Attorney, Agent, or Firm*—Jacobson, Price, Holman & Stern

[57] ABSTRACT

Composition for washing and/or conditioning keratinous substances, containing, in an aqueous medium, 0.1 to 10% by weight, relative to the total weight of the composition, of a copolymer of diallyldialkylammonium units (70–90% by weight) and an acrylic or methacrylic acid (30–10% by weight), and 0.1 to 40% by weight, relative to the total weight of the composition, of an alkyl polyglycoside of formula (I):

$$R(C_6H_{10}O_5)_xH \quad (I)$$

or corresponding to the structural formula (II):

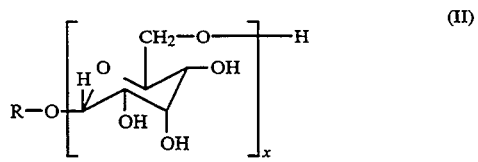

in which:

R denotes an unbranched- or branched-chain $C_8$-$C_{24}$ alkyl or alkenyl radical or a mixture of such radicals; x being a number from 1 to 15, this composition not containing silicone as a conditioning agent or soap as a detergent agent.

15 Claims, No Drawings

COMPOSITIONS FOR CONDITIONING KERATINOUS SUBSTANCES BASED ON ALKYL POLYGLYCOSIDES AND THEIR USE FOR THE WASHING AND CONDITIONING OF HAIR

The present invention relates to compositions for conditioning keratinous substances, and more especially human hair or the skin, based on alkyl polyglycosides and an amphoteric polymer derived from diallyldialkylammonium units and from an acidic monomer chosen from acrylic and methacrylic acids, and to processes for treating keratinous substances employing such compositions.

The invention relates more especially to washing or shampooing compositions, as well to after-shampoo compositions whose application is generally followed by a rinse.

Compositions for washing hair or shampoos are generally formulated from anionic or nonionic surfactants or mixtures thereof, optionally in the presence of amphoteric surfactants.

Used alone, these anionic or nonionic surfactants do not lead to good cosmetic properties and, in particular, the disentangling of wet hair is difficult and the hair feels coarse.

It has been proposed to add cationic polymers and/or silicones to these washing compositions in order to improve their cosmetic properties.

It has, however, been observed that, in an anionic medium, the performance of cationic polymers is not optimal on account of the ionic interaction between the cationic polymer and the anionic surfactant, and problems of stability of the composition sometimes occur.

The introduction of silicone into such solutions based on anionic or nonionic surfactants also creates some problems, in particular in respect of formulation, this also gives rise to problems in respect of the stability of such compositions.

It has also been proposed to incorporate cationic polymers in washing compositions containing alkyl polyglycosides. These detergent compositions present, however, problems of removal on rinsing, and this gives rise to a lack of softness of the dried hair and unsatisfactory disentangling of the wet hair.

In after-shampoo compositions, it has already been proposed in the past to use cationic surfactants and/or cationic polymers, which possess, however, the drawback of accumulating on the hair during successive applications, thereby leading to a weighing down of the hair and imparting an unpleasant feel thereto.

The Applicant has discovered, and this forms the subject of the invention, a composition which enables hair to be conditioned, which can be used for washing or as an after-shampoo and which contains an alkyl polyglycoside and an amphoteric polymer derived from diallyldialkylammonium units and from an acidic monomer chosen from acrylic and methacrylic acids. This composition does not contain silicone as a conditioning agent or soap as a washing agent.

The compositions according to the invention possess, in particular, the feature of being especially stable compared to compositions containing, in addition, a silicone as a conditioning agent.

The compositions according to the invention also possess the advantage of imparting softness and lightness to the treated hair, and enable the hair to dry more rapidly when the composition does not contain soap.

Lastly, these compositions are removed more readily on rinsing and disentangle more readily when the hair is wet.

The subject of the invention is hence a composition for conditioning keratinous substances, in particular hair, which can be used as a shampoo or as an after-shampoo for the purpose of conditioning the treated substances.

The subject of the invention is also a process for washing keratinous substances, and especially hair and the skin, employing such a composition.

Another subject of the invention consists of a process for treatment after shampooing, employing the composition defined above, the application being followed by a rinse.

Other subjects of the invention will become apparent on reading the description and the examples which follow.

The composition for conditioning keratinous substances, and more especially human hair, is essentially characterized in that it contains, in an aqueous medium, from 0.1 to 10% by weight, relative to the total weight of the composition, of a copolymer consisting of 70 to 90% by weight of diallyldialkylammonium units and 30 to 10% by weight of an acidic monomer chosen from acrylic and methacrylic acids, and from 0.1 to 40% by weight, relative to the total weight of the composition, of an alkyl polyglycoside corresponding to the formula:

$$R(C_6H_{10}O_5)_xH \qquad (I)$$

or corresponding as well to the structural formula (II):

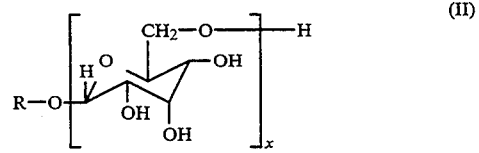

in which:

R denotes an unbranched- or branched-chain $C_8$–$C_{24}$ alkyl or alkenyl radical or a mixture of such radicals, and x is a number from 1 to 15, this composition containing neither silicone as a conditioning agent nor soap as a detergent agent.

The alkyl groups of the diallyldialkylammonium monomer are chosen independently of one another from alkyl groups having 1 to 18 carbon atoms, and preferably represent a methyl or ethyl radical. The molecular weight of the amphoteric polymer defined above is between approximately 50,000 and 10,000,000 determined by gel permeation chromatography, and preferably between 200,000 and 5,000,000. Such polymers are described, more especially, in Application EP-A-0,269,243.

Among these polymers, the copolymers of dimethyldiallylammonium or diethyldiallylammonium chloride and acrylic acid are especially preferred.

There may be mentioned, more especially, the polymer sold under the name MERQUAT 280 by the company CALGON in the form of an aqueous solution containing 35% of active substance, this polymer being a copolymer of diallyldimethylammonium chloride and acrylic acid in the proportions 80:20, the viscosity in a Brookfield LVF viscometer, module 4 at 60 rpm, being between 3.5 Pa. s and 17 Pa. s, the molecular weight being approximately equal to 1,300,000.

The alkyl polyglycosides are chosen, more especially, from the products sold by the company HENKEL under the name APG, such as the products APG 300, APG 350, APG 500, APG 550, APG 625 and APG base 10-12; the products sold by the company SEPPIC under the names TRITON CG 110 (or ORAMIX CG 110) and TRITON CG 312 (or ORAMIX NS 10); and those sold by the company BASF under the name LUTENSOL GD 70.

The preferred alkyl polyglycosides of formula (I) or (II) used according to the invention are APG 300 of the company HENKEL and LUTENSOL GD 70 of the company BASF.

When the compositions according to the invention are used for the washing of keratinous fibres, and more especially hair, the alkyl polyglycoside concentration defined above varies from 1 to 40% by weight, and more preferably from 5 to 30% by weight, relative to the total weight of the composition, and that of the copolymer derived from diallyldialkylammonium units and acrylic or methacrylic acid is preferably between 0.5 and 5% by weight relative to the total weight of the composition.

The washing or shampooing compositions can contain, in addition to the alkyl polyglycoside, other cosurfactants with the exception of soaps. These cosurfactants other than soaps are known per se, and are chosen from anionic, amphoteric, zwitterionic, nonionic and cationic surfactants or mixtures thereof, having detergent properties.

Among anionic surfactants, there may be mentioned the alkali metal salts, ammonium salts, amine salts, amino alcohol salts and magnesium salts of the following compounds: alkyl sulphates, alkyl ether sulphates, alkylamido ether sulphates, alkylaryl polyether sulphates, monoglyceride sulphates; alkylsulphonates, alkylamide sulphonates, alkylarylsulphonates, olefin sulphonates, paraffin sulphonates; alkyl sulphosuccinates, alkyl ether sulphosuccinates, alkylamide sulphosuccinates; alkyl sulphosuccinamates; alkyl sulphoacetates; alkyl ether phosphates; acyl sarcosinates, N-acyltaurates.

The alkyl or acyl radical of these different compounds generally consists of a carbon chain containing from 10 to 20 carbon atoms.

It is also possible to use weakly anionic surfactants such as polyoxyalkylenated ether carboxylic acids, such as those containing 2 to 50 ethylene oxide groups.

The nonionic surfactants other than those of the formula (I) are chosen, more especially, from polyethoxylated, polypropoxylated or polyglycerolated alcohols or α-diols or alkylphenols or fatty acids, having a fatty chain containing 8 to 18 carbon atoms, the number of ethylene oxide or propylene oxide groups being between 2 and 50 and the number of glycerol groups being between 2 and 30.

There may be mentioned, more especially, copolymers of ethylene oxide and propylene oxide; condensates of ethylene oxide and propylene oxide with fatty alcohols; polyethoxylated fatty amides preferably having 2 to 30 mol of ethylene oxide; polyglycerolated fatty amides preferably containing 1 to 5 glycerol groups and especially 1.5 to 4 glycerol groups; polyethoxylated fatty amines preferably having 2 to 30 mol of ethylene oxide; oxyethylenated fatty acid esters of sorbitan preferably having 2 to 30 mol of ethylene oxide; fatty acid esters of sugar, fatty acid esters of polyethylene glycol, fatty acid esters of glycols, amine oxides such as the oxides of ($C_{10}$-$C_{14}$ alkyl)amines or of N-acylamidopropylmorpholine.

Preferred amphoteric or zwitterionic surfactants are derivatives of secondary or tertiary aliphatic amines in which the aliphatic radical is a linear or branched chain containing 8 to 18 carbon atoms and which contains at least one carboxylate, sulphonate, sulphate, phosphate or phosphonate anionic group conferring water-solubility; ($C_8$-$C_{20}$ alkyl)betaines, sulphobetaines, ($C_8$-$C_{20}$ alkyl)amido($C_1$-$C_6$ alkyl)betaines or ($C_8$-$C_{20}$ alkyl)amido($C_1$-$C_6$ alkyl)sulphobetaines.

Among amine derivatives, there may be mentioned the products marketed under the name MIRANOL, such as those described in U.S. Pat. Nos. 2,528,378 and 2,781,354 or classified in the CTFA Dictionary, 3rd edition, 1982, under the names Amphocarboxyglycinates or Amphocarboxypropionates.

The cosurfactants are used in the washing compositions according to the invention in sufficient proportions to impart, in combination with the alkyl polyglycoside necessarily present in these compositions, a detergent character to the composition. These cosurfactants are generally present in proportions of between 0.5 and 30% by weight relative to the total weight of the composition, and especially between 1 and 20% by weight.

The compositions according to the invention can also contain other agents, and more especially foam enhancers or "boosters" such as fatty acid alkanolamides, and in particular those derived from coconuts.

When the compositions according to the invention are used as after-shampoo compositions, their application is generally followed by a rinse. In these compositions, the concentration of alkyl polyglycoside varies from 0.1 to 10%, and preferably from 0.3 to 5%, by weight relative to the total weight of the composition, and the concentration of copolymer of diallyldialkylammonium units and acrylic or methacrylic acid varies from 0.1 to 10%, and preferably from 0.3 to to 5%, by weight relative to the total weight of the composition. They can contain anionic cosurfactants excluding amphoteric, nonionic or cationic soaps, defined above, these agents being present in proportions of between approximately 0.05 and 5% by weight, and preferably from 0.1 to 3% by weight, relative to the total weight of the composition.

In the conditioning compositions applied after washing to keratinous substances, it is preferable to use nonionic or cationic cosurfactants.

Among nonionic cosurfactants, it is preferable to use fatty acid esters of sugars, and among cationic surfactants, it is preferable to use ($C_{16}$-$C_{22}$ alkyl)trimethylammonium chlorides and quaternary ammonium salts such as the product designated QUATERNIUM 27 in the CTFA, 4th edition, sold under the name REWOQUAT 75 PG by the company REWO.

The compositions according to the invention can also contain adjuvants customarily used in cosmetic compositions, and in particular compositions for shampooing or conditioning hair.

To this end, there may be mentioned thickening agents, preservatives, perfumes and, where appropriate, fats such as fatty alcohols, hydrocarbon waxes or oils.

In a particular embodiment, it is possible to use, in particular in after-shampoos according to the invention, a mixture of alkyl polyglycoside and cetyl/stearyl alcohol such as the product marketed under the name MONTANOL 68.

It is also possible to add synthetic organic oils such as isoparaffins, for instance, more especially, the product sold under the name ARLAMOL HD by the company ICI, to these conditioning or washing compositions.

The compositions according to the invention may be used in various forms such as liquid, thickened liquid, gel or cream form, and, where appropriate, be packaged as an aerosol and dispensed in the form of a foam.

The process for washing and/or conditioning keratinous substances, and especially hair, according to the invention, consists in applying to these substances at least one composition as is defined above, this application being followed by a step of rinsing with water.

The washing compositions may be used as shampoos, but also as a shower gel for washing hair and the skin, in which case they are applied to the wet hair and skin, which are rinsed after application.

When the compositions are used for the conditioning of hair, they are applied to wet hair washed beforehand with a conventional shampoo or one according to the invention. After an exposure time of 1 to 10 minutes, the hair is rinsed with water. It is found that the wet hair disentangles well, dries rapidly and is light even after several treatments.

The examples which follow are intended to illustrate the invention, no limitation, however, being implied.

EXAMPLES

EXAMPLE 1

A shampoo of the following composition is prepared:

| | |
|---|---|
| Alkyl ($C_9/C_{10}/C_{11}$, 20:40:40) (1→4) -polyglycoside sold at a concentration of 50% of AS under the name APG 300 by the company HENKEL | 18 g AS |
| Copolymer of diallyldimethylammonium chloride and acrylic acid, sold under the name MERQUAT 280 by the company CALGON at a concentration of 35% of AS | 0.6 g AS |
| Heptamethylnonane sold under the name ARLAMOL HD by the company ICI | 1.8 g |
| Ethers of hexadecanediol (3 mol) and of polyethylene glycol (60 mol of ethylene oxide) | 2.5 g |
| Preservative qs | |
| Hydrochloric acid qs pH 7 | |
| Water | qs 100 g |

EXAMPLE 2

A shampoo of the following composition is prepared:

| | |
|---|---|
| Alkyl ($C_9/C_{10}/C_{11}$, 20:40:40) (1→4) -polyglycoside sold at a concentration of 50% of AS under the name APG 300 by the company HENKEL | 12 g AS |
| Urethane polyether sold under the name DAPRAL T212 by the company AKZO | 1.5 g |
| Copolymer of diallyldimethylammonium chloride and acrylic acid, sold under the name MERQUAT 280 by the company CALGON at a concentration of 35% of AS | 2.5 g AS |
| Ethers of hexadecanediol (3 mol) and of polyethylene glycol (60 mol of ethylene oxide) | 2.5 g |
| Preservative qs | |
| Triethanolamine qs pH 6.7 | |
| Water | qs 100 g |

EXAMPLE 3

A shampoo of the following composition is prepared:

| | |
|---|---|
| Alkyl ($C_9/C_{10}/C_{11}$, 20:40:40) (1→4) -polyglycoside sold at a concentration of 50% of AS under the name APG 300 by the company HENKEL | 5 g AS |
| Copolymer of diallyldimethylammonium chloride and acrylic acid, sold under the name MERQUAT 280 by the company CALGON at a concentration of 35% of AS | 0.25 g AS |
| Amphoteric surfactant designated "Cocoamphocarboxyglycinate" in the CTFA Dictionary, 3rd edition, 1982, sold at a concentration of 38% of AS under the name MIRANOL C2M conc. by the company MIRANOL | 5 g AS |
| Derivative of dioleate of polyethylene glycol (55 mol of ethylene oxide) and of propylene glycol, sold under the name ANTIL 141 Liquid by the company GOLDSCHMIDT at a concentration of 43.6% of AS | 1.5 g AS |
| Preservative qs | |
| Hydrochloric acid qs pH 7.6 | |
| Water | qs 100 g |

EXAMPLE 4

A shampoo of the following composition is prepared:

| | |
|---|---|
| Alkyl ($C_9/C_{10}/C_{11}$, 20:40:40) (1→4) -polyglycoside sold at a concentration of 50% of AS under the name APG 300 by the company HENKEL | 20 g AS |
| Copolymer of diallyldimethylammonium chloride and acrylic acid, sold under the name MERQUAT 280 by the company CALGON at a concentration of 35% of AS | 4.5 g AS |
| Ethers of hexadecanediol (3 mol) and of polyethylene glycol (60 mol of ethylene oxide) | 2.5 g |
| Coconut acid monoisopropanolamide | 2.5 g |
| Preservative qs | |
| Triethanolamine qs pH 6 | |
| Water | qs 100 g |

EXAMPLE 5

An after-shampoo of the following composition is prepared:

| | |
|---|---|
| Alkyl ($C_9/C_{10}/C_{11}$, 20:40:40) (1→4) -polyglycoside sold at a concentration of 50% of AS under the name APG 300 by the company HENKEL | 2 g AS |
| Copolymer of diallyldimethylammonium chloride and acrylic acid, sold under the name MERQUAT 280 by the company CALGON at a concentration of 35% of AS | 3 g AS |
| Mixture (80:20) of cetyl/stearyl alcohol and oxyethylenated cetyl/stearyl alcohol containing 33 mol of ethylene oxide, sold under the name SINNOWAX AO by the company HENKEL | 2 g |
| Cetyl alcohol | 1 g |
| Stearyl alcohol | 1 g |
| Hydroxyethylcellulose sold under the name | 1 g |

-continued

| | |
|---|---|
| NATROSOL 250 HHR by the company AQUA-LON | |
| Preservative qs | |
| Triethanolamine qs pH 5 | |
| Water | qs 100 g |

EXAMPLE 6

An after-shampoo of the following composition is prepared:

| | |
|---|---|
| Mixture (23:77 by weight) of cetyl/stearyl glycoside and cetyl/stearyl alcohol, sold under the name MONTANOL 68 by the company SEPPIC | 8 g |
| Copolymer of diallyldimethylammonium chloride and acrylic acid, sold under the name MERQUAT 280 by the company CALGON at a concentration of 35% of AS | 2 g AS |
| Glycerol | 1.5 g |
| Preservative qs | |
| Triethanolamine qs pH 5 | |
| Water | qs 100 g |

EXAMPLE 7

A shampoo of the following composition is prepared:

| | |
|---|---|
| Alkyl ($C_9/C_{10}/C_{11}$, 20:40:40) (1→4) -polyglycoside sold at a concentration of 50% of AS under the name APG 300 by the company HENKEL | 15 g AS |
| Copolymer of diallyldimethylammonium chloride and acrylic acid, sold under the name MERQUAT 280 by the company CALGON at a concentration of 35% of AS | 1 g AS |
| Water | qs 100 g |

The pH is adjusted to 7 with triethanolamine.

This composition, used as a shampoo, enables hair to be readily disentangled.

EXAMPLE 8

A shampoo of the following composition is prepared:

| | |
|---|---|
| PLANTAREN 1200 CS UP: alkyl polylgucoside in which the alkyl group is a $C_{12}/C_{14}/C_{16}$ mixture | 5 g AS |
| Mixture of glycerides of palm POE (200 EO) and coprah (7 EO) | 2 g AS |
| MERQUAT 280 | 0.35 g AS |
| Water | qs 100 g |
| HCl qs pH 6.5 | |

We claim:

1. Composition for washing and/or conditioning keratinous substances and skin, containing, in an aqueous medium, 0.1 to 10% by weight, relative to the total weight of the composition, of a copolymer consisting of 70 to 90% by weight of diallyldialkylammonium units and 30 to 10% by weight of an acrylic acid or methacrylic acid acidic monomer, and 0.1 to 40% by weight, relative to the total weight of the composition, of an alkyl polyglycoside of the formula (I):

$$R(C_6H_{10}O_5)_xH \qquad (I)$$

or corresponding to the structural formula (II):

$$\begin{array}{c}(II)\end{array}$$

in which:

R denotes an unbranched- or branched-chain $C_8$–$C_{24}$ alkyl or alkenyl radical or a mixture of such radicals; x being a number from 1 to 15, said composition not containing silicone as a conditioning agent or soap as a detergent agent.

2. Composition according to claim 1, wherein the molecular weight of the copolymer of diallyl dialkylammonium units and acrylic or methacrylic acid is between 50,000 and 10,000,000 determined by gel permeation chromatography.

3. Composition according to claim 1, wherein the copolymer of diallyldialkylammonium units and acrylic or methacrylic acid is a copolymer of dimethyldiallylammonium chloride or diethyl diallylammonium chloride and acrylic acid having a molecular weight of between 200,000 and 5,000,000.

4. Composition according to claim 1 wherein the alkyl polyglycoside is an alkyl ($C_9/C_{10}/C_{11}$) polyglycoside.

5. Composition according to claim 1 wherein the composition contains cosurfactants having detergent properties other than soaps, selected from the group consisting of anionic, amphoteric, zwitterionic, nonionic surfactants other than those of formula (I), cationic surfactants and mixtures thereof.

6. Composition according to claim 5, wherein the composition contains cosurfactants present in proportions of between 0.5 and 30% by weight relative to the total weight of the composition.

7. Composition according to claim 6, wherein the composition contains cosurfactants present in proportions of between 1 and 20% by weight.

8. Composition according to claim 1 used for the washing of keratinous substances and/or the skin, wherein the alkyl polyglycoside is present in proportions ranging from 1 to 40%, by weight relative to the total weight of the composition, and wherein the copolymer of diallyldialkylammonium units and acrylic acid or methacrylic acid is present in proportions of between 0.5 and 5% by weight.

9. Composition according to claim 8, wherein the alkyl polyglycoside is present in proportions ranging from 5 to 30% by weight relative to the total weight of the composition.

10. Hair conditioning composition, according to claim 1 wherein the composition contains 0.1 to 10% by weight of the alkyl polyglycoside, and 0.3 to 5% by weight of the copolymer of diallyldialkylammonim units and acrylic acid or methacrylic acid.

11. Composition according to claim 10, wherein the composition contains cationic or nonionic cosurfactants.

12. Composition according to claim 1, wherein the composition contains thickening agents, preservatives, perfumes or fats selected from the group consisting of fatty alcohols, hydrocarbon waxes and oils.

13. Composition according to claim 1, wherein the composition contains a mixture of alkyl polyglycoside and cetyl/stearyl alcohol.

14. Process for washing keratinous substance and/or the skin, comprising applying a composition as defined in claim 1 to the keratinous substance, wherein the keratinous substance is hair, and/or skin and then rinsing the hair and/or skin with water.

15. Process for treatment of keratinous substance after it is washed wherein the keratinous substance is hair, comprising applying a composition as defined in claim 1 to the wet hair, and rinsing the hair, after an exposure time of 1 minute to 10 minutes.

* * * * *